US007396860B2

(12) United States Patent
Blaugrund et al.

(10) Patent No.: US 7,396,860 B2
(45) Date of Patent: Jul. 8, 2008

(54) USE OF RASAGILINE WITH OR WITHOUT RILUZOLE TO TREAT AMYOTROPHIC LATERAL SCLEROSIS

(75) Inventors: Eran Blaugrund, Rehovot (IL); Ruth Levy, Tel-Aviv (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 541 days.

(21) Appl. No.: 10/712,958

(22) Filed: Nov. 13, 2003

(65) Prior Publication Data

US 2004/0127577 A1 Jul. 1, 2004

Related U.S. Application Data

(60) Provisional application No. 60/426,543, filed on Nov. 15, 2002.

(51) Int. Cl.
*A61K 31/13* (2006.01)
(52) U.S. Cl. .................................................. 514/647
(58) Field of Classification Search .................. 514/647
See application file for complete search history.

(56) References Cited

U.S. PATENT DOCUMENTS

| | | | |
|---|---|---|---|
| 3,513,249 | A | 5/1970 | Gittos et al. |
| 5,387,612 | A | 2/1995 | Youdim et al. |
| 5,444,095 | A | 8/1995 | Tatton et al. |
| 5,453,446 | A | 9/1995 | Youdim et al. |
| 5,457,133 | A | 10/1995 | Youdim et al. |
| 5,486,541 | A | 1/1996 | Sterling et al. |
| 5,519,061 | A | 5/1996 | Youdim et al. |
| 5,527,814 | A | 6/1996 | Louvel |
| 5,532,415 | A | 7/1996 | Youdim et al. |
| 5,576,353 | A | 11/1996 | Youdim et al. |
| 5,599,991 | A | 2/1997 | Youdim et al. |
| 5,668,181 | A | 9/1997 | Youdim et al. |
| 5,744,500 | A | 4/1998 | Youdim et al. |
| 5,767,164 | A | 6/1998 | Tatton et al. |
| 5,786,390 | A | 7/1998 | Youdim et al. |
| 5,844,003 | A | 12/1998 | Tatton et al. |
| 5,891,923 | A | 4/1999 | Youdim et al. |
| 6,126,968 | A | 10/2000 | Peskin et al. |
| 6,277,886 | B1 | 8/2001 | Levy et al. |
| 6,316,504 | B1 | 11/2001 | Youdim et al. |
| 6,630,514 | B2 | 10/2003 | Youdim et al. |
| 6,635,667 | B2 | 10/2003 | Thomas |
| 6,956,060 | B2 | 10/2005 | Youdim et al. |
| 2004/0010038 | A1 | 1/2004 | Blaugrund et al. |
| 2004/0052843 | A1 | 3/2004 | Lerner et al. |
| 2005/0093830 | A1 | 5/2005 | Youdim et al. |
| 2006/0018957 | A1 | 1/2006 | Lerner et al. |
| 2006/0094783 | A1 | 5/2006 | Youdim et al. |
| 2006/0188581 | A1 | 8/2006 | Peskin |

FOREIGN PATENT DOCUMENTS

| | | |
|---|---|---|
| WO | 0538134 | 4/1993 |
| WO | 0436492 | 6/1994 |
| WO | WO95/11016 | * 4/1995 |
| WO | 9518617 | 7/1995 |
| WO | 9637199 | 11/1996 |
| WO | 9712583 | 4/1997 |
| WO | 9802152 | 1/1998 |
| WO | WO03072055 | 9/2003 |
| WO | WO2004045515 | 6/2004 |
| WO | 2006057912 | 6/2006 |

OTHER PUBLICATIONS

Kaal et al. Chronic mitochondrial inhibition induces selective motoneuron death in vitro: a new model for amyotrophic lateral sclerosis. Journal of Neurochemistry, 2000, 74(3) pp. 1158-1165.*

Orru et al. Association of monoamine oxidase B alleles with age at onset in amyotrophic lateral sclerosis. Neuromuscular Disorder 9 (1999) pp. 593-597.*

Turner MR, et al., (2001) The King's data base 1990-2000: An analysis of the effect on survival of interventions in ALS. *ALS and Other Motor Neuron Disorders*, 2(Suppl. 2):43; and.

Traynor BJ, et al., (2001) Riluzole and prognosis in amyotrophic lateral sclerosis: Findings of the Irish amyotrophic lateral sclerosis register over a five year study period 1995-2000. *ALS and Other Motor Neuron Disorders*, 2(Suppl. 2):43-4.

Wong PC, et al., (1995) An adverse property of a familial ALS-linked SOD1 mutation causes motor neuron diseases characterized by vacuolar degeneration of mitochondria. *Neuron*, 14:1105-16.

Bensimon G, et al., (1994) A controlled trial of riluzole in amyotrophic lateral sclerosis. ALS/Riluzole Study Group. *N Engl J Med.*, 330(9):585-91.

Bentué-Ferrer D, et al., (1996) Monoamine Oxidase B Inhibitors. *CNS Drugs.*, 6(3):217-36.

Doble A. (1996) The pharmacology and mechanism of action riluzole. *Neurology*, 47 (Suppl. 1):S233-41.

Eliash S, et al. (2001) Rasagiline and its (S) enantiomer increase survival and prevent stroke in salt-loaded stroke-prone spontaneously hypertensive rats. *J. Neural Transm.*,108:909-23.

Ferrante RJ, et al., (1997) Increased 3-nitrotyrosine and oxidative damage in mice with a human copper/zinc superoxide dismutase mutation. *Ann. Neurol.*, 42:326-34.

(Continued)

*Primary Examiner*—Jennifer Kim
(74) *Attorney, Agent, or Firm*—John P. White; Cooper & Dunham LLP

(57) ABSTRACT

The subject invention provides a method for treating amyotrophic lateral sclerosis (ALS) in a subject in need of such treatment comprising administering to the subject R(+)-N-propargyl-1-aminoindan or a pharmaceutically acceptable salt thereof alone or in combination with 2-amino-6-trifluoromethoxy benzothiazole in amounts effective to treat ALS in the subject.

12 Claims, 2 Drawing Sheets

OTHER PUBLICATIONS

Figure 1:
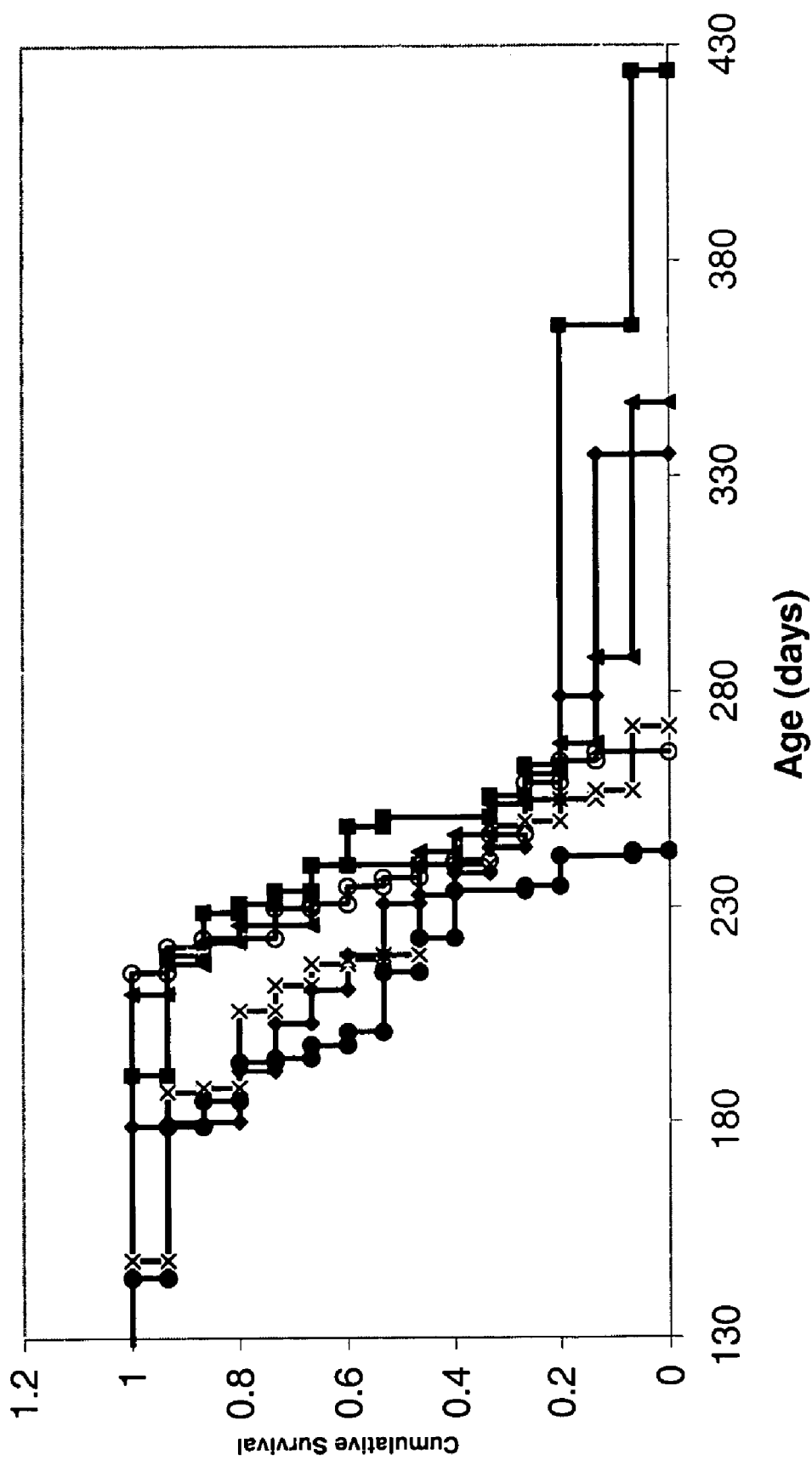

"Guidance for Industry: In vivo drug metabolism/drug interaction studies—study design, data analysis, and recommendations for dosing and labeling," U.S. Department of Health and Human Services, Food and Drug Administration, Center for Drug Evaluation and Research (CDER), Center for Biologics Evaluation and Research (CBER), Nov. 1999.

Gurney ME, et al., (1994) Motor neuron degeneration in mice that express a human superoxide dismutase mutation. *Science*, 264:1772-5.

Gurney ME, et al., (1996) Benefit of vitamin E, riluzole, and gabapentin in a transgenic model of familial amyotrophic lateral sclerosis. *Ann. Neurol.*, 39:147-57.

Huang W, et al., (1999) Neuroprotective effect of rasagiline, a selective monoamine oxidase-B inhibitor, against closed head injury in the mouse. *Eur. J. Pharmacol.*, 336:127-35.

Kong J, et al., (1998) Massive mitochondrial degeneration in motor neurons triggers the onset of amyotrophic lateral sclerosis in mice expressing a mutant SOD1. *J. Neurosci.*, 18:3241-50.

Lacomblez L, et al., (1996) Dose-ranging study of riluzole in amyotrophic lateral sclerosis. *Lancet*, 347:1425-31.

Lange DJ, et al., (1998) Selegiline is ineffective in a collaborative double-blind, placebo-controlled trial for treatment of amyotrophic lateral sclerosis. *Arch Neurol.*, 55(1):93-6.

Ludolph AC, et al., (1999) Antiglutamate therapy in ALS—which is the next step? *J. Neural Transm.*, 55(Suppl.):79-96.

Maruyama W, et al., (2000) Neurotoxins induce apoptosis in dopamine neurons: protection by N-propargylamine-1(R)- and (S)-aminoindan, rasagiline and TV1022. *J. Neural Transm.*, 60(Suppl):171-86.

Maruyama W, et al. (2001) Transfection-enforced bcl-2 overexpression and an anti-Parkinson drug, rasagiline, prevent nuclear accumulation of glyceraldehyde-3-phosphate dehydrogenase induced by an endogenous dopaminergic neurotoxin, N-methyl(R)salsolinol. *J. Neurochem.*, 78:727-35.

Physicians Desk Reference (2002), p. 772-5.

Speiser Z, et al., (1999) Studies with rasagiline, a monamine oxidase-B inhibitor, in experimental focal ischemia in the rat. *J. Neural Transm.*, 106:593-606.

Traynor BJ, et al., (2001) Riluzole and prognosis in amyotrophic lateral sclerosis: Findings of the Irish amyotrophic lateral sclerosis register over a five year study period 1995-2000. *ALS and Other Motor Neuron Disorders*, 2(Suppl. 2):43-4.

Turner MR, et al., (2001) The King's data base 1990-2000: An analysis of the effect on survival of interventions in ALS. *ALS and Other Motor Neuron Disorders*, 2(Suppl. 2):43.

Vielhaber S, et al., (2000) Mitochondrial DNA abnormalities in skeletal muscle patients with sporadic amyotrophic lateral sclerosis. *Brain*, 123:1339-48.

Wong PC, et al., (1995) An adverse property of a familial ALS-linked SOD1 mutation causes motor neuron diseases characterized by vacuolar degeneration of mitochondria. *Neuron*, 14:1105-16; and.

Youdim MBH, et al., (2001) Rasagiline (N-propargyl-1R(+)-aminoindan), a selective and potent inhibitor of mitochondrial monoamine oxidase B *Br. J. Pharmacol.*, 132:500-6.

U.S. Appl. No. 11/595,726, filed Nov. 10, 2006, Youdim et al.

U.S. Appl. No. 11/600,561, filed Nov. 15, 2006, Frenkel et al.

Finberg et al., (1981) "Selective Irreversible Propargyl Derivative Inhibitors of Monoamine Oxidase (MAO) without the Cheese Effect" *Chem. Abstracts* 94:202499.

Finberg and Youdim, (1985) "Modification of Blood Pressure and Nictitating Membrane Response to Sympathetic Amines by Selective Monoamine Oxidase Inhibitors" *Brit. J. Pharmac.* 541-546.

Finberg et al. (1985) "Modification of Blood Pressure and Nictitating Membrane Response to Sympathetic Amides by Selective Monoamide Oxidase Inhibitors, Type A and B, in the Cat" *Chem. Abstracts* 103:81618.

Mendleicz and M.B.H. Youdim (1987) *Brit. J. Psychiat*, 142:508-511.

Youdim et al.(1984) *Progress in Medical Chemistry* 21:138-167.

Youdim et al. (1988) Handbook of Experimental Pharmacology vol. 90/I (1988) Chapter 3 Trendlenburg and Weiner, eds.

Munsat, T.L. (1981) "Amantadine and guanidine are ineffective in ALS" *Neurology* 31:1054.

Naoi, M. et al. "Mitochondrial Permeability Transition Pores: A Target of Apoptosis Regulation by Rasagiline", Abstracts of the Society for Neuroscience, Society for Neuroscience, Washington, DC, US, vol. 27, No. 1, p. 520, XP001189217.

Supplemental European Search Report of European Application No. EP 03 78 3422, date of completion Apr. 8, 2008.

\* cited by examiner

USE OF RASAGILINE WITH OR WITHOUT RILUZOLE TO TREAT AMYOTROPHIC LATERAL SCLEROSIS

This application claims the benefit of U.S. Provisional Application No. 60/426,543, filed Nov. 15, 2002, the entire contents of which are hereby incorporated by reference.

Throughout this application various publications are referenced in parenthesis. Full citations for these publications may be found listed in alphabetical order at the end of the specification immediately preceding the claims. The disclosures of these publications in their entireties are hereby incorporated by reference into this application in order to more fully describe the state of the art to which this invention pertains.

BACKGROUND OF THE INVENTION

Amyotrophic lateral sclerosis (ALS), also known as Lou Gehrig's disease, is a neurodegenerative disease that occurs when motor neurons degenerate, causing the muscles under their control to atrophy (Amyotrophic Lateral Sclerosis Information Page, National Institute of Neurological Disorders and Stroke). Symptoms may include loss of motor control in one's extremities, twitching, cramping and difficulties in speaking, swallowing and breathing. Death usually occurs within 5 years of diagnosis. Neuroprotective treatment of patients suffering from ALS is in its early stages (Ludolph, A. C. et al.). The etiology and pathogenesis of ALS are not known, although a number of hypotheses have been advanced (Physician's Desk Reference, 2002) One hypothesis is that motor neurons, made vulnerable through either genetic predisposition or environmental factors, are injured by glutamate (Id.). There is evidence that mitochondrial damage and oxidative stress plays a role in human sporadic ALS (Ludolph A. C. et al.; Vielhaber S. et al.). In some cases of familial ALS, the enzyme superoxide dismutase has been found to be defective (Physician's Desk Reference, 2002).

Currently, transgenic mice carrying multiple copies of the human G93A mutation are considered to be the best model system for anterior horn cell degenerations such as ALS (Ludolph A. C. et al.; Gurney M. E. et al., *Science* (1994); Gurney M. E. et al., *Ann. Neurol.* (1996)). In this model the cell degeneration is caused by a biological factor responsible for the etiology of the disease in some patients. The model is well-characterized on the morphological and functional level and is comparatively robust.

Neuropathological studies of the G93A mice support current ideas stressing that mitochondrial damage and oxidative stress are important pathogenetic factors for anterior horn cell disease since mitochondrial swelling and vacuolization are among the earliest pathologic features observed (Ferrante R. J. et al.; Wong P. C. et al.; Kong J. et al.). There is evidence that this mechanism also plays a role in human sporadic ALS (Ludolph A. C. et al.; Vielhaber S. et al.).

Riluzole, a membrane-stabilizing drug, has been shown to have a therapeutic effect on ALS. Riluzole is a member of the benzothiazole class (*Physician's Desk Reference*, (2002)). Chemically, riluzole is 2-amino-6-trifluoromethoxy benzothiazole and has a molecular formula of $C_8H_5F_3N_2OS$ (Id.). Its structural formula is as follows:

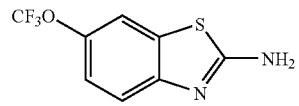

It has a molecular weight of 234.2. Pharmacological properties of riluzole include an inhibitory effect on glutamate release (Id.) mediated by inactivation of voltage-dependent sodium channels and by its ability to interfere with intracellular events that follow transmitter binding at excitatory amino acid receptors.

RILUTEK®, which has been FDA-approved for the treatment of ALS, is a capsule-shaped, white, film-coated tablet for oral administration containing 50 mg of riluzole. The recommended dose for RILUTEK® is 50 mg every 12 hours. (*Physician's Desk Reference*, (2002), p. 772-775, the entire contents of which are hereby incorporated by reference.)

Rasagiline has been shown to have certain neuroprotective effects. Rasagiline has the chemical name R(+)-N-propargyl-1-aminoindan and its structural formula is:

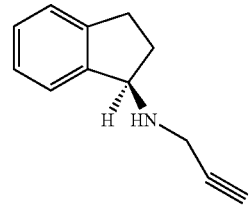

Rasagiline is believed to reduce oxidative stress by inhibition of monoamine oxidase B (MAO-B) (Youdim M. B. H. et al.). However, neuroprotection with rasagiline has also been linked to apoptosis, presumably by a bcl-2-like effect on the mitochondrial membrane potential (Maruyama W. et al.). Neuroprotection with rasagiline has been demonstrated in stroke models (Speiser Z. et al.; Eliash S. et al.) and in models of traumatic head injury (Huang W. et al.). However, rasagiline has not been suggested to be effective for the treatment of ALS.

Rasagiline, its salts, preparation and use for the treatment of Parkinson's disease, memory disorders and other neurological disorders have been the subject of numerous patents, including U.S. Pat. Nos. 5,387,612, 5,453,446, 5,457,133, 5,668,181, 5,576,353, 5,532,415, 5,599,991, 5,786,390, 5,519,061, 5,891,923, 5,744,500 and 6,316,504, the contents of which are incorporated by reference.

The in vivo interactions between two drugs, such as those of the subject invention, are complex. The effects of a drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug ("Guidance for Industry"). Thus, when two drugs are administered to treat the same disease, it is unclear whether each will complement the therapeutic activity of the other, have no effect, or interfere with the therapeutic activity of the other.

Not only may the interaction between two drugs affect the intended therapeutic activity of each drug, but the interaction may increase the levels of toxic metabolites ("Guidance for Industry"). The interaction may also heighten or lessen the side effects of each drug.

Additionally, it is difficult to predict when the effects of the interaction between the two drugs will become manifest. For example, metabolic interactions between drugs may become apparent upon the initial administration of the second drug, after the two have reached a steady-state of concentration or even upon discontinuation of one of the drugs ("Guidance for Industry").

Thus, the success of one drug or each drug separately in an in vitro model, an animal model or even in humans may not translate into success of the administration of both drugs in humans.

The present invention presents the unexpected discovery that rasagiline is effective for the treatment of ALS. Also disclosed is that the combination of rasagiline with riluzole is more effective for treating ALS than either drug alone. In particular, the results of rasagiline used in G93A mice alone or in combination with riluzole indicated that oral administration of rasagiline produced a dose-dependent improvement in motor performance and convincingly extended survival in these mice.

SUMMARY OF THE INVENTION

The subject invention provides a method for treating amyotrophic lateral sclerosis (ALS) in a subject in need of such treatment comprising administering to the subject R(+)-N-propargyl-1-aminoindan or a pharmaceutically acceptable salt thereof in an amount effective to treat ALS in the subject.

The subject invention further provides a method for treating amyotrophic lateral sclerosis (ALS) in a subject in need of such treatment comprising administering to the subject an amount of R(+)-N-propargyl-1-aminoindan or a pharmaceutically acceptable salt thereof and an amount of 2-amino-6-trifluoromethoxy benzothiazole, wherein the total amount is effective to treat ALS in the subject.

The subject invention further provides a pharmaceutical composition comprising R(+)-N-propargyl-1-aminoindan or a pharmaceutically acceptable salt thereof, 2-amino-6-trifluoromethoxy benzothiazole and a pharmaceutically acceptable carrier.

The subject invention further provides a package comprising a pharmaceutically acceptable preparation of R(+)-N-propargyl-1-aminoindan or a pharmaceutically acceptable salt thereof, a separate pharmaceutically acceptable preparation of 2-amino-6-trifluoromethoxy benzothiazole, and instructions for use of the preparations in the treatment of amyotrophic lateral sclerosis (ALS).

DETAILED DESCRIPTION OF THE FIGURES

FIG. 1: Survival curves (Kaplan-Meier) for each group of SOD1 transgenic mice. (x=rasagiline 0.5 mg/kg; ○=rasagiline 2.0 mg/kg; ◆=riluzole 30 mg/kg; ▲=rasagiline 0.5 mg/kg+riluzole 30 mg/kg; ■=rasagiline 2.0 mg/kg+riluzole 30 mg/kg; ●=control).

Figure 2:
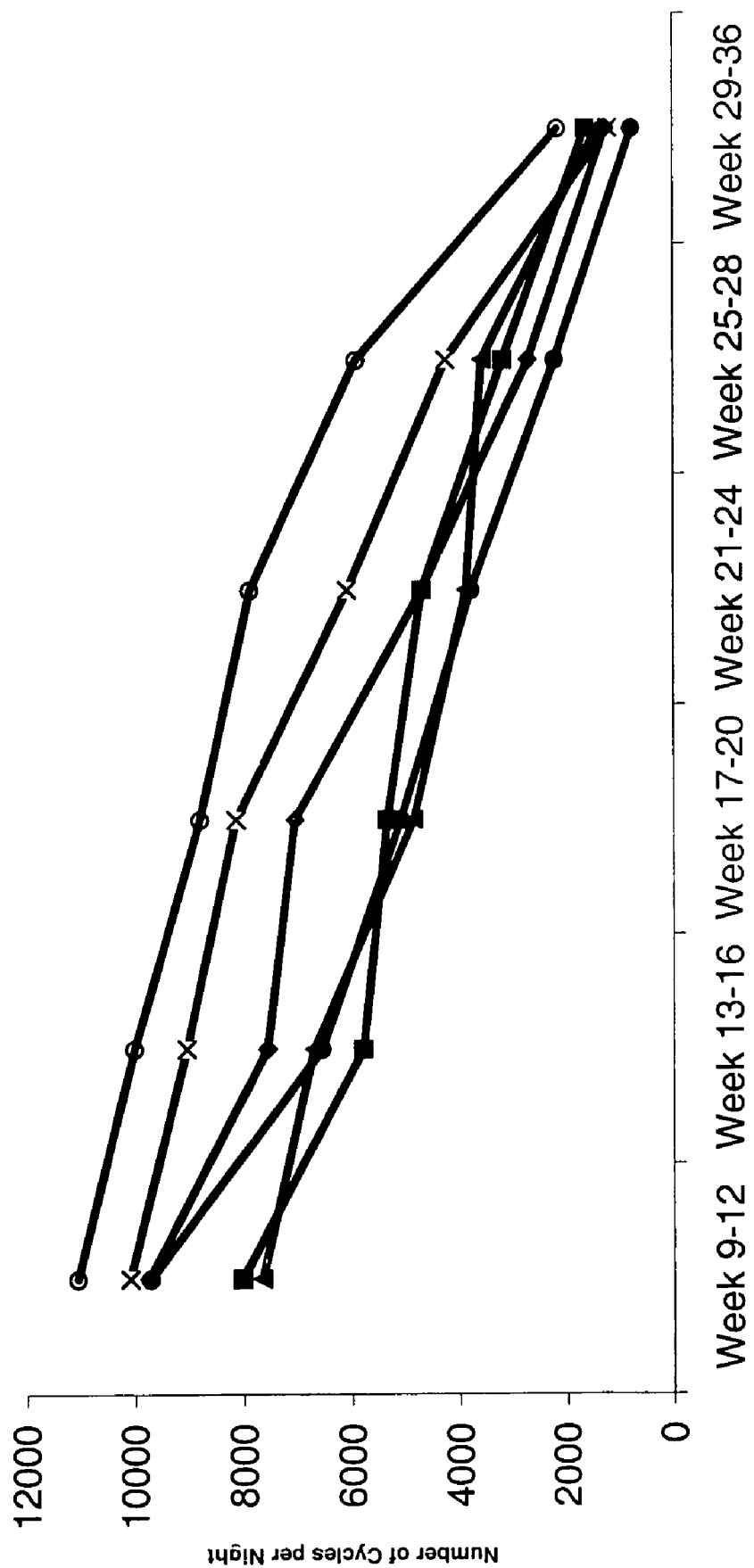

FIG. 2: Effects of rasagiline and/or riluzole in different doses on rotarod activity of SOD1 transgenic mice. (x=rasagiline 0.5 mg/kg; ○=rasagiline 2.0 mg/kg; ◆=riluzole 30 mg/kg; ▲=rasagiline 0.5 mg/kg+riluzole 30 mg/kg; ■=rasagiline 2.0 mg/kg+riluzole 30 mg/kg; ●=control).

DETAILED DESCRIPTION OF THE INVENTION

The subject invention provides a method for treating amyotrophic lateral sclerosis (ALS) in a subject in need of such treatment comprising administering to the subject R(+)-N-propargyl-1-aminoindan or a pharmaceutically acceptable salt thereof in an amount effective to treat ALS in the subject.

In one embodiment of the above method, the pharmaceutically acceptable salt is the chloride, mesylate, maleate, fumarate, tartarate, hydrochloride, hydrobromide, esylate, p-toluenesulfonate, benzoate, acetate, phosphate or sulfate salt.

In a further embodiment, the pharmaceutically acceptable salt is the mesylate salt.

In another embodiment, the effective amount of R(+)-N-propargyl-1-aminoindan is from about 0.1 to about 20 mg.

In another embodiment, the method further comprises administering 2-amino-6-trifluoromethoxy benzothiazole in an amount effective to treat ALS in the subject.

The subject invention also provides a method for treating amyotrophic lateral sclerosis (ALS) in a subject in need of such treatment comprising administering to the subject an amount of R(+)-N-propargyl-1-aminoindan or a pharmaceutically acceptable salt thereof and an amount of 2-amino-6-trifluoromethoxy benzothiazole, wherein the amounts when administered together are effective to treat ALS in the subject.

In one embodiment of the above method, the pharmaceutically acceptable salt is the chloride, mesylate, maleate, fumarate, tartarate, hydrochloride, hydrobromide, esylate, p-toluenesulfonate, benzoate, acetate, phosphate or sulfate salt.

In another embodiment of the method, the pharmaceutically acceptable salt is the mesylate salt.

In a further embodiment, the amount of R(+)-N-propargyl-1-aminoindan or a pharmaceutically acceptable salt thereof is effective to treat ALS when administered alone, and the amount of 2-amino-6-trifluoromethoxy benzothiazole is effective to treat ALS when administered alone.

In a further embodiment, the administration of R(+)-N-propargyl-1-aminoindan or a pharmaceutically acceptable salt thereof and 2-amino-6-trifluoromethoxy benzothiazole is substantially concurrent.

In a further embodiment, R(+)-N-propargyl-1-aminoindan or a pharmaceutically acceptable salt thereof is administered and then 2-amino-6-trifluoromethoxy benzothiazole is administered.

In a further embodiment, the effective amount of R(+)-N-propargyl-1-aminoindan or a pharmaceutically acceptable salt thereof is from about 0.1 to about 20 mg and the effective amount of 2-amino-6-trifluoromethoxy benzothiazole is from about 5 to about 500 mg.

In one embodiment, the method comprises administering from about 0.001 mg to about 20 mg of R(+)-N-propargyl-1-aminoindan, alone or in combination with 2-amino-6-trifluoromethoxy benzothiazole, from about 5 mg to about 500 mg.

In another embodiment, the method comprises administering from about 1.6 mg to about 2.4 mg of R(+)-N-propargyl-1-aminoindan or 2.0 mg of R(+)-N-propargyl-1-aminoindan, from about 3 mg to about 5 mg of R(+)-N-propargyl-1-aminoindan, 8.0 mg to about 16.0 mg of R(+)-N-propargyl-1-aminoindan, 12.0 mg to about 16.0 mg of R(+)-N-propargyl-1-aminoindan, 16.0 mg to about 20 mg of R(+)-N-propargyl-1-aminoindan, 7.2 mg to about 8.8 mg of R(+)-N-propargyl-1-aminoindan, or about 8.0 mg of R(+)-N-propargyl-1-aminoindan, alone or in combination with about 5 mg to about 500 mg of 2-amino-6-trifluoromethoxy benzothiazole.

In a further embodiment, the method comprises administering any of the above dosages of R(+)-N-propargyl-1-aminoindan in combination with from about 25 mg to about 65 mg of 2-amino-6-trifluoromethoxy benzothiazole, from about 65 mg to about 150 mg of 2-amino-6-trifluoromethoxy benzothiazole, from about 150 mg to about 300 mg of 2-amino-6-trifluoromethoxy benzothiazole, from about 300 mg to about 500 mg of 2-amino-6-trifluoromethoxy benzothiazole, from about 25 mg to about 35 mg of 2-amino-6-trifluoromethoxy benzothiazole, from about 45 mg to about 55 mg of 2-amino-6-trifluoromethoxy benzothiazole, or from about 35 mg to about 65 mg of 2-amino-6-trifluoromethoxy benzothiazole.

The subject invention also provides a pharmaceutical composition comprising R(+)—N-propargyl-1-aminoindan or a pharmaceutically acceptable salt thereof, 2-amino-6-trifluoromethoxy benzothiazole and a pharmaceutically acceptable carrier.

In one embodiment, the pharmaceutical composition is formulated for oral, topical, parenteral or nasal administration.

The subject invention further provides a package comprising the pharmaceutical composition and instructions for use of the pharmaceutical composition in the treatment of amyotrophic lateral sclerosis (ALS).

The subject invention further provides a package comprising a pharmaceutically acceptable preparation of R(+)-N-propargyl-1-aminoindan or a pharmaceutically acceptable salt thereof, a separate pharmaceutically acceptable preparation of 2-amino-6-trifluoromethoxy benzothiazole, and instructions for use of the preparations in the treatment of amyotrophic lateral sclerosis (ALS).

The subject invention further provides the use of R(+)-N-propargyl-1-aminoindan or a pharmaceutically acceptable salt thereof for manufacturing a medicament useful for treating amyotrophic lateral sclerosis (ALS) in a subject.

In one embodiment of the above use, the pharmaceutically acceptable salt is the chloride, mesylate, maleate, fumarate, tartarate, hydrochloride, hydrobromide, esylate, p-toluenesulfonate, benzoate, acetate, phosphate or sulfate salt.

In another embodiment, the pharmaceutically acceptable salt is the mesylate salt.

In another embodiment of the above use, the medicament further comprises 2-amino-6-trifluoromethoxy benzothiazole.

The subject invention further provides the use of R(+)-N-propargyl-1-aminoindan or a pharmaceutically acceptable salt thereof for manufacturing a first medicament in a package having instructions for administration of the first medicament to treat amyotrophic lateral sclerosis (ALS) in a subject.

In one embodiment of the above use, the pharmaceutically acceptable salt is the chloride, mesylate, maleate, fumarate, tartarate, hydrochloride, hydrobromide, esylate, p-toluenesulfonate, benzoate, acetate, phosphate or sulfate salt.

In another embodiment, the pharmaceutically acceptable salt is the mesylate salt.

In another embodiment of the above use, the package separately comprises a second medicament which comprises 2-amino-6-trifluoromethoxy benzothiazole and instructions for administration of the second medicament to treat ALS in the subject.

The subject invention further provides R(+)-N-propargyl-1-aminoindan or a pharmaceutically acceptable salt thereof for use in treating amyotrophic lateral sclerosis (ALS).

In one embodiment, the pharmaceutically acceptable salt is the chloride, mesylate, maleate, fumarate, tartarate, hydrochloride, hydrobromide, esylate, p-toluenesulfonate, benzoate, acetate, phosphate or sulfate salt for use in treating amyotrophic lateral sclerosis (ALS).

In another embodiment, the pharmaceutically acceptable salt is the mesylate salt, for use in treating amyotrophic lateral sclerosis (ALS).

The subject invention further provides R(+)—N-propargyl-1-aminoindan or a pharmaceutically acceptable salt thereof for use in treating amyotrophic lateral sclerosis (ALS) in combination with 2-amino-6-trifluoromethoxy benzothiazole.

In one embodiment, the pharmaceutically acceptable salt is the chloride, mesylate, maleate, fumarate, tartarate, hydrochloride, hydrobromide, esylate, p-toluenesulfonate, benzoate, acetate, phosphate or sulfate salt for use in treating amyotrophic lateral sclerosis (ALS) in combination with 2-amino-6-trifluoromethoxy benzothiazole.

In another embodiment, the pharmaceutically acceptable salt is the mesylate salt, for use in treating amyotrophic lateral sclerosis (ALS) in combination with 2-amino-6-trifluoromethoxy benzothiazole.

Pharmaceutically acceptable salts include, but are not limited to, mesylate, maleate, fumarate, tartarate, hydrochloride, hydrobromide, esylate, p-toluenesulfonate, benzoate, acetate, phosphate and sulfate salts.

Formulations of the present invention include those suitable for oral administration. The formulations may conveniently be presented in unit dosage form and may be prepared by any methods well known in the art of pharmacy. The amount of active ingredient or ingredients which can be combined with a carrier material to produce a single dosage form will generally be that amount of the compound(s) which produce(s) a therapeutic effect as discussed herein.

Methods of preparing these formulations or compositions include the step of bringing into association a compound or combination of the present invention with the carrier and, optionally, one or more accessory ingredients. In general, the formulations are prepared by uniformly and intimately bringing into association the active compound or compounds with liquid carriers, or finely divided solid carriers, or both, and then, if necessary, shaping the product.

Formulations of the invention suitable for oral administration may be in the form of capsules, pills, tablets, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) each containing a predetermined amount of the active compound or compounds.

In solid dosage forms of the invention for oral administration (capsules, tablets, pills, dragees, powders, granules and the like), the active ingredient(s) is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient(s) therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient(s) can also be in micro-encapsulated form, if appropriate, with one or more of the above-described excipients.

Liquid dosage forms for oral administration of the active ingredients include pharmaceutically acceptable emulsions, microemulsions, solutions, suspensions, syrups and elixirs. In addition to the active ingredient(s), the liquid dosage forms may contain inert dilutents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert dilutents, the oral compositions can also include adjuvants such as wetting agents, emulsifying and suspending agents, sweetening, flavoring, coloring, perfuming and preservative agents.

Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The preparations of the present invention may be given orally, parenterally, topically, or rectally. They are of course given by forms suitable for each administration route. For example, they are administered in tablets or capsule form, by injection, inhalation, ointment, suppository, etc. administration by injection, infusion or inhalation; topical by lotion or ointment; and rectal by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The invention is further illustrated by the following examples which in no way should be construed as being further limiting. The contents of all references, pending patent applications and published patent applications, cited throughout this application, including those referenced in the background section, are hereby incorporated by reference. It should be understood that the models used throughout the examples are accepted models and that the demonstration of efficacy in these models is predictive of efficacy in humans.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Example 1

Animals

Transgenic mice overexpressing human Cu/Zn-SOD G93A mutations ((B6SJL-TgN (SOD1-G93A) 1 Gur) and non-transgenic B6/SJL mice were purchased from Jackson Laboratories (Ben Harbor, Me., USA). The second generation of G1H mice were used for this study; a group of animals which in our hands has a mean survival time of about 200 days (first generation 130 days). Animals were maintained and bred in the animal facility of the University of Ulm. The transgenic progeny were identified by amplification of mouse tail DNA by the polymerase chain reaction.

Treatment Protocol

The SOD1 transgenic mice were treated in five groups (N=15) with two dosages of rasagiline alone or in combination with riluzole. Another group of 15 mice served as controls.

Treatment protocols for the six groups were the following:
Group I: Rasagiline 0.5 mg/kg per day
Group II: Rasagiline 2.0 mg/kg per day
Group III: Riluzole 30 mg/kg per day
Group IV: Rasagiline 0.5 mg/kg and Riluzole 30 mg/kg per day
Group V: Rasagiline 2.0 mg/kg and Riluzole 30 mg/kg per day
Group VI: Controls The drugs were administered by drinking water starting at 60 days of age. The daily dosages were calculated based on a daily water intake of 6 ml. Fresh solutions were prepared once a week with the total consumed volume measured in order to ensure a constant daily and weekly dose. Water intake was not different between the groups and was in the range of the expected 6 ml. This was confirmed by comparing the water intake of the controls and the treated animals. Similarly, longitudinal measurements did not reveal major changes in dosing, even in late stages of the disease. The study was done blindly, meaning that the treatment and the preparation of the drugs were conducted by separate individuals.

Behaviour and Weight Assessment

Mice were observed daily (including weekends) and weighed weekly. Motor performance was assessed from 40 days of age using the rotarod apparatus to measure the night activity of the mice from 8 p.m.-8 a.m. (LMTB, Berlin). The activity of the animals was recorded individually by a computerized system and assessed daily, including weekends. For statistical evaluation, the rotarod activity was normalized to the mean activity of each animal from day 40 to day 60.

Survival

The clinical condition of the mice was monitored daily starting at 40 days. The onset of clinical signs was scored by examining the mice for tremors and/or shaking of the limbs, and the position of one or both hind limbs (hanging rather than splaying out) when the mice were suspended in the air by their tail. The age of clinical onset was determined by the age (days) at which loss of splay or tremors of hind limbs were observed. Examining the mice for the loss of righting reflex determined the end stage of the disease. The mice were sacrificed if they could not right themselves within 30 seconds when placed on either side on a flat surface. This decision was made by an independent veterinarian as requested by the animal protocol. The treatment protocol was approved by the Regierungspräsident Tübingen (35/9185.81-3). The treatment and clinical evaluation were conducted by separate individuals, and thus the neurological signs for determining onset and end stage of disease were scored in a blinded manner.

Statistics

Data are expressed as the mean +/−standard error of the mean (SEM). Rotarod testing and weight were compared by analysis of variance (ANOVA). Survival data were analysed by the Mantel-Cox proportional hazard model. Statistical significance was tested by one-way ANOVA followed by post-hoc Student-Newman-Keuls comparison with the SPSS-PC software program (SPSS, Chicago Ill.).

Neuropathological Studies

Mice were perfused transcordially with 4% paraformaldehyde. Brains and whole spinal cord were dissected out, frozen in liquid nitrogen and cut in transverse sections of 20 μm on a sliding microtome. Sections of brainstem and spinal cord were stained with HE, toluidin blue (semi-thin sections, 0.5 μm), and immunohistochemistry to label astrocytes (GFAP), cholinergic motoneurons (CHAT) and dopaminergic cells (TH).

Results

Survival

The primary end point of this study was survival as defined by the animal protocol. The mean life expectancy of each of the groups is shown in table 1. FIG. 1 shows the complementary Kaplan-Meier curves. Controls had an average life expectancy of 210.9 days (Standard Error of the Means, SEM=7.4779) whereas riluzole-treated animals died after 233.6 days (SEM=12.6034). Partially due to the comparatively large SEM, this difference was only close to the $p=0.05$ level of significance. Animals treated with the low dose of rasagiline alone (0.5 mg/kg/day) survived 223.8667 (SEM=8.5037) days; this extension of survival was not statistically significant. The larger dose of rasagiline increased life span by 29 days (life expectancy 239.8667; SEM=4.4281); this result was statistically significant ($p<0.001$). We observed a dose-dependent effect of rasagiline as shown by the Mantel-Cox proportional hazard model. The largest extension of life span was observed with the combination of both riluzole and rasagiline. This effect was also dose-dependent since mean age of death was 247.8667 (SEM=7.9089) days with the combination of 0.5 mg/kg/day rasagiline whereas in the 2.0 mg/kg/day rasagiline combination group life span was extended to 252.0 (SEM=9.4047) days. Both results were shown to be statistically different from the controls ($p<0.001$; $p<0.001$), and from the group treated with riluzole alone ($p<0.02$; $p<0.03$).

TABLE 1

Statistics of the effects of rasagiline and riluzole on cumulative survival in SOD1 transgenic mice

| | | Mean | |
| --- | --- | --- | --- |
| | N | Survival (days) | Std. Error |
| RA0.5 | 15 | 223.8667 | 8.5037 |
| RA2 | 15 | 239.8677 | 4.4281 |
| RI30 | 15 | 233.6000 | 12.6034 |
| RIRA0.5 | 15 | 247.8667 | 7.9089 |
| RIRA2 | 15 | 252.0000 | 9.4047 |
| CONTROL | 15 | 210.9333 | 7.4779 |

(RA0.5 = rasagiline 0.5 mg/kg; RA2 = rasagiline 2.0 mg/kg; RI30 = riluzole 30 mg/kg; RIRA0.5 = rasagiline 0.5 mg/kg + riluzole 30 mg/kg; RIRA2 = rasagiline 2.0 mg/kg + riluzole 30 mg/kg)

Running Wheel Activity

The results of measurements of running wheel activity in the 6 groups were largely complementary to the survival data, but we also observed apparently independent pharamacological effects (FIG. 2). The differences between groups were seen early in the preclinical period and differences of function persisted until late in the disease. Statistical analysis showed that rasagiline-(with both dosages) and riluzole-treated animals were more active during the course of treatment and also seemed to maintain their motor activity longer when compared to controls (Table 2). However, the motor activity of the groups treated with either low-dose or high-dose rasagiline combined with riluzole was lower—contrasting with the increased survival time.

More specifically, we observed a significantly decreased running wheel activity of both groups treated with rasagiline combined with riluzole. When compared with untreated animals, the decreased activity was already observed during weeks 9 to 12 ($p=0.01$; $p=0.04$). During weeks 13 and 16 the running wheel activity of the groups treated with rasagiline alone was significantly increased when compared with the motor activity of the control group ($p=0.007$; $p=0.0003$). This increased activity remained stable until week 29. At week 29, the motor performance of the group treated with low-dose rasagiline began to decrease and only the group treated with high-dose rasagiline was still significantly more active ($p=0.01$, weeks 29-36). There was no case of premature death in any of the groups and we did not observe any signs of overt toxicity of either rasagiline alone or the riluzole/rasagiline combination.

Since the rasagiline/riluzole combination groups survived longer than all the other groups (see above), but had decreased motor activity, additional factors other than those associated with neuroprotection must be responsible for the decreased motor activity. Without limiting ourselves to any specific theory, we believe that one possible explanation could be that the combination has a slight sedative effect on the animals.

However, this sedation was not seen during daily observation and had no impact on weight gain or intake of drinking water.

TABLE 2

Statistics of the effects of rasagiline and riluzole on running wheel activity in SOD1 transgenic mice

|  | Weeks 9-12 | Weeks 13-16 | Weeks 17-20 | Weeks 21-24 | Weeks 25-28 | Weeks 29-36 |
|---|---|---|---|---|---|---|
| RA0.5 | 10087 | 9037.14 | 8124.12 | 6070.08 | 4236.96 | 1196.69 |
| RA2 | 11056 | 9999.44 | 8787.09 | 7873.22 | 5902.76 | 2147.29 |
| RI30 | 9729.58 | 7556.57 | 7033.85 | 4687.05 | 2696.11 | 1249.13 |
| RIRA0.5 | 7653.71 | 6692.88 | 4840.69 | 3856.61 | 3558.49 | 1410.11 |
| RIRA2 | 8019.22 | 5775.98 | 5339.56 | 4687.97 | 3165.95 | 1626.65 |
| Control | 9710.04 | 6545.52 | 5079.64 | 3764.38 | 2201.02 | 766.28 |

(RA0.5 = rasagiline 0.5 mg/kg; RA2 = rasagiline 2.0 mg/kg; RI30 = riluzole 30 mg/kg; RIRA0.5 = rasagiline 0.5 mg/kg + riluzole 30 mg/kg; RIRA2 = rasagiline 2.0 mg/kg + riluzole 30 mg/kg)

Discussion

We examined the neuroprotective effect of the MAO-B inhibitor and antiapoptotic compound rasagiline alone and in combination with the putative glutamate release blocker riluzole in the G93A model of familial amyotrophic lateral sclerosis (fALS). The drug had a convincing dose-dependent therapeutic effect on both, preclinical and clinical motor function and survival of the animals. We also found that the combination of rasagiline with riluzole is safe and increased survival by about 20% in a dose-dependent manner.

The mechanism of action of riluzole is thought to be related to its stabilizing effect on sodium channels and the resulting reduction of presynaptic glutamate release (Doble, A.); the neuroprotective effect of rasagiline is likely to be independent of inhibition of MAO-B and due to a bcl-2-like stabilizing effect of the mitochondrial membrane potential (Maruyama, W. et al., (2001) *J. Neurochem.*; Maruyama, W. et al., (2000) *J. Neural Trans.*).

Although riluzole is considered the first drug with a neuroprotective effect in amyotrophic lateral sclerosis, there is universal agreement that the riluzole effect should be improved. In the present study, we have shown that a combination of the MAO-B inhibitor rasagilirne and riluzole dose-dependently increases the life span of G93A mice considerably. These drugs also have a beneficial and dose-dependent effect on motor function. However, during early treatment, there was no effect of the drug combinations on motor function. Without limiting ourselves to any particular theory, we consider the lack of early functional effects of the combination treatment regimens as a consequence of a non-specific pharmacological effect on either behaviour or motor activity or both. We did not observe other side or toxic effects of the drugs employed. The validity of our results is underlined by the partial reproduction of the riluzole effect (Gurney M. E. et al., *Ann. Neurol.* (1996)).

In our view, the interpretation of the results of these studies is only limited by the known drawbacks of the G93A model. These drawbacks and how they are addressed by the present study listed below.

It is well-known that the life expectancy of the mice used in the present study increases in subsequent generations. In order to account for this factor we consistently used the F2 generation. Thus, we do not consider variation caused by this factor a serious problem.

Similarly, the variation of life expectancy within a single generation is also not a serious consideration for the interpretation of the results of this study since the treatment effect was comparably large. However, without limiting ourselves to any particular theory, we believe that this variation is the cause of the observation that the riluzole effect (mean survival 234 days) is not statistically significant in our study although it is of a similar order of magnitude as the riluzole effect previously observed by others (Gurney M. E. et al., *Ann. Neurol.* (1996)) and ourselves (unpublished results). In addition, we believe that the lack of a formal statistical effect of the low-dose rasagiline group (mean survival 224 days) is partially explained by this variance. We consider this variation normal.

In order to account for the fact that even within the same generation the interindividual variation of motor activity is relevant, we normalized the motor activity measurements before statistical analysis.

Finally, it is often pointed out that measurement of survival time has its pitfalls and due to different levels of animal care, treatment results as reported in the literature may not be comparable. However, we do not consider this factor significant for the outcome of this study since sacrifice of the animals was not the decision of the investigators but that of an independent veterinarian who was not involved in the study.

The disclosed study, therefore, shows that the combination of rasagiline and riluzole is an effective clinical combination for the treatment of ALS.

Those skilled in the art will recognize, or be able to ascertain, using no more than routine experimentation, many equivalents to specific embodiments of he invention described specifically herein. Such equivalents are intended to be encompassed in the scope of the following claims.

REFERENCES

Doble A. "The pharmacology and mechanism of action of riluzole." *Neurology* 1996;47(Suppl. 1):S233-241.

Eliash S, Speiser Z, Cohen S. "Rasagiline and its (S) enantiomer increase survival and prevent stroke in salt-loaded stroke-prone spontaneously hypertensive rats." *J. Neural Transm.* 2001;108:909-923.

Ferrante R J, Shinobu L A, Schulz J B, et al. "Increased 3-nitrotyrosine and oxidative damage in mice with a human copper/zinc superoxide dismutase mutation." *Ann. Neurol.* 1997;42:326-334.

"Guidance for Industry: In vivo drug metabolism/drug interaction studies—study design, data analysis, and recommendations for dosing and labeling," U.S. Department of Health and Human Services, Food and Drug Administration, Center for Drug Evaluation and Research (CDER), Center for Biologics Evaluation and Research (CBER), November 1999.

Gurney M E, Pu H, Chiu A Y, et al "Motor neuron degeneration in mice that express a human superoxide dismutase mutation." *Science* 1994;264:1772-1775.

Gurney M E, Cutting F B, Zhai P, et al. "Benefit of vitamin E, riluzole, and gabapentin in a transgenic model of familial amyotrophic lateral sclerosis. *Ann. Neurol.* 1996;39:147-157.

Huang W, Chen Y, Shohani E, Weinstock M. "Neuroprotective effect of rasagiline, a selective monoamine oxidase-B inhibitor, against closed head injury in the mouse." *Eur. J. Pharmacol.* 1999;336:127-135.

Kong J, Xu Z. "Massive mitochondrial degeneration in motor neurons triggers the onset of amyotrophic lateral sclerosis in mice expressing a mutant SOD1." *J. Neurosci.* 1998;18:3241-3250.

Lacomblez L, Bensimon G, Leigh P N, et al. "Dose-ranging study of riluzole in amyotrophic lateral sclerosis." *Lancet* 1996;347:1425-1431.

Ludolph A C, Meyer T, Riepe M W. "Antiglutamate therapy in ALS—which is the next step?" *J. Neural Transm.* 1999; (Suppl.) 55:79-96.

Maruyama W, Akao Y, Youdim M B H, Naoi M. "Neurotoxins induce apoptosis in dopamine neurons: protection by N-propargylamine-1(R)- and (S)-aminoindan, rasagiline and TV1022." *J. Neural Transm.* 2000;(Suppl) 60:171-186.

Maruyama W, Akao Y, Youdim M B H, David B A, Naoi M. "Transfection-enforced bcl-2 overexpression and an anti-Parkinson drug, rasagiline, prevent nuclear accumulation of glyceraldehyde-3-phosphate dehydrogenase induced by an endogenous dopaminergic neurotoxin, N-methyl(R)salsolinol." *J. Neurochem.* 2001;78:727-735.

Speiser Z, Mayk A, Eliash S, Cohen S. "Studies with rasagiline, a monoamine oxidase-B inhibitor, in experimental focal ischemia in the rat." *J. Neural Transm.* 1999;106:593-606.

Traynor B J, Alexander M, Corr B, et al. "Riluzole and prognosis in amyotrophic lateral sclerosis: Findings of the Irish amyotrophic lateral sclerosis register over a five year study period 1995-2000." *ALS and other motor neuron disorders* 2001;2(Suppl. 2):43-44.

Turner M R, Bakker M, Sham P, et al. "The King's data base 1990-2000: An analysis of the effect on survival of interventions in ALS." *ALS and other motor neuron disorders* 2001;2 (Suppl. 2):43.

Vielhaber S, Kunz D, Winkler K, et al. "Mitochondrial DNA abnormalities in skeletal muscle of patients with sporadic amyotrophic lateral sclerosis." *Brain* 2000;123:1339-1348.

Wong P C, Pardo Calif., Borchelt D R et al. "An adverse property of a familial ALS-linked SOD1 mutation causes motor neuron disease characterized by vacuolar degeneration of mitochondria." *Neuron* 1995;14:1105-1116.

Youdim M B H, Gross A, Finberg J P M. "Rasagiline (N-propargyl-1R(+)-aminoindan), a selective and potent inhibitor of mitochondrial monoamine oxidase B." *Br. J. Pharmacol.* 2001; 132:500-506.

What is claimed is:

1. A method for treating amyotrophic lateral sclerosis (ALS) in a subject in need of such treatment comprising administering to the subject R(+)-N-propargyl-1-aminoindan or a pharmaceutically acceptable salt thereof in an amount effective to treat ALS in the subject.

2. The method of claim 1, wherein the pharmaceutically acceptable salt is the chloride, mesylate, maleate, fumarate, tartarate, hydrochloride, hydrobromide, esylate, p-toluenesulfonate, benzoate, acetate, phosphate or sulfate salt.

3. The method of claim 2, wherein the pharmaceutically acceptable salt is the mesylate salt.

4. The method of claim 1, wherein the effective amount of R(+)-N-propargyl-1-aminoindan is from about 0.1 to about 20 mg.

5. The method of claim 1, further comprising administering 2-amino-6-trifluoromethoxy benzothiazole in an amount effective to treat ALS in the subject.

6. A method for treating amyotrophic lateral sclerosis (ALS) in a subject in need of such treatment comprising administering to the subject an amount of R(+)-N-propargyl-1-aminoindan or a pharmaceutically acceptable salt thereof and an amount of 2-amino-6-trifluoromethoxy benzothiazole, wherein the amounts when administered together are effective to treat ALS in the subject.

7. The method of claim 6, wherein the pharmaceutically acceptable salt is the chloride, mesylate, maleate, fumarate, tartarate, hydrochloride, hydrobromide, esylate, p-toluenesulfonate, benzoate, acetate, phosphate or sulfate salt.

8. The method of claim 7, wherein the pharmaceutically acceptable salt is the mesylate salt.

9. The method of claim 6, wherein the amount of R(+)-N-propargyl-1-aminoindan or a pharmaceutically acceptable salt thereof is effective to treat ALS when administered alone, and the amount of 2-amino-6-trifluoromethoxy benzothiazole is effective to treat ALS when administered alone.

10. The method of claim 6, wherein the administration of R(+)-N-propargyl-1-aminoindan or a pharmaceutically acceptable salt thereof and 2-amino-6-trifluoromethoxy benzothiazole is concurrent.

11. The method of claim 6, wherein R(+)-N-propargyl-1-aminoindan or a pharmaceutically acceptable salt thereof is administered and then 2-amino-6-trifluoromethoxy benzothiazole is administered.

12. The method of claim 6, wherein the effective amount of R(+)-N-propargyl-1-aminoindan or a pharmaceutically acceptable salt thereof is from about 0.1 to about 20 mg and the effective amount of 2-amino-6-trifluoromethoxy benzothiazole is from about 5 to about 500 mg.

* * * * *